United States Patent
Katayama et al.

(10) Patent No.: US 10,428,183 B2
(45) Date of Patent: Oct. 1, 2019

(54) ROOM TEMPERATURE-CURABLE RESIN COMPOSITION CONTAINING AN ALUMINUM CHELATE COMPOUND

(71) Applicant: SHIN-ETSU CHEMICAL CO., LTD., Tokyo (JP)

(72) Inventors: Taiki Katayama, Annaka (JP); Takahiro Yamaguchi, Annaka (JP); Takafumi Sakamoto, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 16/267,652

(22) Filed: Feb. 5, 2019

(65) Prior Publication Data

US 2019/0169373 A1 Jun. 6, 2019

Related U.S. Application Data

(62) Division of application No. 14/891,030, filed as application No. PCT/JP2014/062047 on May 1, 2014, now abandoned.

(30) Foreign Application Priority Data

May 16, 2013 (JP) ................... 2013-104046
Jul. 8, 2013 (JP) ................... 2013-142645

(51) Int. Cl.
| | | |
|---|---|---|
| *C08G 77/08* | (2006.01) | |
| *B01J 31/22* | (2006.01) | |
| *C09K 3/10* | (2006.01) | |
| *C07F 5/06* | (2006.01) | |
| *C09D 183/04* | (2006.01) | |
| *C09J 183/04* | (2006.01) | |
| *C08L 83/04* | (2006.01) | |
| *C08K 5/00* | (2006.01) | |
| *C08G 77/18* | (2006.01) | |
| *C08G 77/20* | (2006.01) | |

(52) U.S. Cl.
CPC ............. *C08G 77/08* (2013.01); *B01J 31/22* (2013.01); *C07F 5/069* (2013.01); *C08K 5/0091* (2013.01); *C08L 83/04* (2013.01); *C09D 183/04* (2013.01); *C09J 183/04* (2013.01); *C09K 3/1018* (2013.01); *C08G 77/18* (2013.01); *C08G 77/20* (2013.01)

(58) Field of Classification Search
CPC ......... C08G 77/08; C08G 77/18; C08G 77/20
USPC ........................................................ 528/16
See application file for complete search history.

(56) References Cited

U.S. PATENT DOCUMENTS

| 3,463,800 A * | 8/1969 | Kroll ................. C07F 5/066 526/189 |
|---|---|---|
| 4,111,890 A | 9/1978 | Getson et al. |
| 4,437,959 A * | 3/1984 | Hayase .................. C08G 59/68 522/12 |
| 5,585,445 A * | 12/1996 | Meguriya ............ C08G 59/226 525/476 |
| 2004/0001970 A1 | 1/2004 | Qiu et al. |
| 2008/0319152 A1* | 12/2008 | Okamoto ............. C08G 65/336 528/25 |
| 2010/0249338 A1 | 9/2010 | Kamiya |
| 2011/0257324 A1 | 10/2011 | Ziche et al. |

FOREIGN PATENT DOCUMENTS

| CN | 101925628 | | 12/2010 |
|---|---|---|---|
| EP | 1 876 201 A1 | | 1/2008 |
| JP | 39-27643 | | 12/1964 |
| JP | 58-88225 | * | 7/1979 |
| JP | 55-43119 A | | 3/1980 |

(Continued)

OTHER PUBLICATIONS

English language translation JP 54-088225 (Year: 1979).*

(Continued)

*Primary Examiner* — Margaret G Moore
(74) *Attorney, Agent, or Firm* — Birch, Stewart, Kolasch & Birch, LLP

(57) ABSTRACT

Provided is a room temperature-curable resin composition containing an aluminum chelate compound. This aluminum chelate compound is an aluminum chelate compound having a β-dicarbonyl compound represented by the following general formula (1):

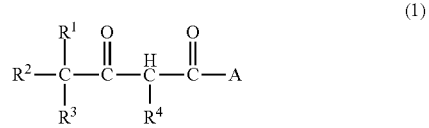

wherein each of $R^1$ to $R^3$ represents a monovalent hydrocarbon group or a halogen atom; $R^4$ represents a hydrogen atom or a monovalent hydrocarbon group; and A is a group selected from a group represented by the following formula (2) and a group represented by —$OR^8$:

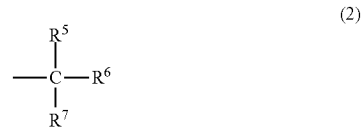

wherein each of $R^5$ to $R^7$ represents a monovalent hydrocarbon group or a halogen atom; and $R^8$ represents a monovalent hydrocarbon group.

16 Claims, 3 Drawing Sheets

(56) References Cited

FOREIGN PATENT DOCUMENTS

| JP | 57-10622 | A | 1/1982 |
|---|---|---|---|
| JP | 62-225344 | A | 10/1987 |
| JP | 5-262989 | A | 10/1993 |
| JP | 7-39547 | B2 | 5/1995 |
| JP | 7-331076 | A | 12/1995 |
| JP | 11-199855 | A | 7/1999 |
| JP | 2001-214268 | A | 8/2001 |
| JP | 2004-162002 | A | 6/2004 |
| JP | 3850969 | B2 | 11/2006 |
| JP | 2012-511607 | A | 5/2012 |

OTHER PUBLICATIONS

Atwood et al., "Bimetallic Aluminium and Gallium Derivatives of 1,1,1,5,5,5-Hexafluoropentane-2,4-dione via Selective Metallation/Hydrometallation", Journal of the Chemical Society Dalton Transactions, 1994, No. 13, pp. 2019-2021.

Bouyahyi et al., "Aluminum Complexes of Fluorinated β-Diketonate Ligands: Syntheses, Structures, Intramolecular Reduction, and Use in Ring-Opening Polymerization of Lactide", Organometallics, 2010, vol. 29, pp. 491-500.

Chinese Office Action issued in Chinese Patent Application No. 201480028399.2 dated Aug. 26, 2016.

Database WPI Week 198209 Thomson Scientific, London, GB: AN 1982-16340E, XP002763780 (JP S57-10622 A).

Database WPI Week 200213 Thomson Scientific, London, GB: AN 2002-092335, XP002763781 (JP 2001 214268 A).

Extended European Search Report dated Nov. 14, 2016, in European Patent Application No. 14797162.6.

Hudson et al., "Photochemical deposition and characterization of Al2O3 and TiO2", Journal of Materials Research, Nov./Dec. 1988, vol. 3, No. 6, pp. 1151-1157.

International Search Report, issued in PCT/JP2014/062047, dated Jul. 29, 2014.

Kumar et al., "Synthesis, Spectral Studies and Antifungal Activity of β-Diketonate Complexes of Bimetallic Organotin(IV) aluminium(III)-μ-oxoalkoxides", Asian Journal of Chemistry, 2007, vol. 19, No. 5, pp. 3869-3876.

Notification of Grounds for Rejection dated Jun. 7, 2016, in Japanese Patent Application No. 2013-104046, with English translation.

Pickering et al., "Kinetics, Steric Course, and Mechanism of Stereoisomerization of Aluminum β-Diketonates", Journal of the American Chemical Society, 1976, vol. 98, No. 15, pp. 4503-4515.

Trundle et al., "Precursors for Thin Film Oxides by Photo-MOCVD", Applied Surface Science, 1989, vol. 36, pp. 102-118.

* cited by examiner

ROOM TEMPERATURE-CURABLE RESIN COMPOSITION CONTAINING AN ALUMINUM CHELATE COMPOUND

CROSS REFERENCE TO RELATED APPLICATIONS

This application is a Divisional of copending application Ser. No. 14/891,030, filed on Nov. 13, 2015, which is a national phase of PCT International Application No. PCT/JP2014/062047 filed on May 1, 2014, which claims the benefit under 35 U.S.C. § 119(a) to Patent Application No. 2013-104046, filed in Japan on May 16, 2013 and Patent Application No. 2013-142645, filed in Japan on Jul. 8, 2013, all of which are hereby expressly incorporated by reference into the present application.

TECHNICAL FIELD

The present invention relates to an aluminum chelate compound useful as, for example, a catalyst of a room temperature-curable resin; and a room temperature-curable resin composition containing the same. Particularly, the present invention relates to a room temperature-curable organopolysiloxane composition as well as a molded product obtained by curing such composition.

BACKGROUND ART

A β-diketo compound enabling keto-enol transformation is capable of forming a complex compound with aluminum in an enol structure. That is, there is produced an aluminum chelate compound as a compound containing a β-diketo group(s). Because an alkyl group(s) bonded to a β-diketo group(s) is usually included in a β-diketo compound, such aluminum chelate compound also has an affinity for many kinds of organic polymeric materials. For this reason, such aluminum chelate compound has been used in compositions containing organic polymeric materials, such as paints, adhesive agents and inks, and has endowed these compositions with various types of properties. For example, such aluminum chelate compound is used as a catalytic composition for a room temperature-curable resin.

As such a kind of aluminum chelate compound, there has been known, for example, a monoacetylacetonate aluminum bis (ethylacetoacetate) 76% isopropanol solution. Patent document 1 discloses, for example, a method for synthesizing such aluminum chelate compound. However, such known aluminum chelate compound often exhibits a low activity when used as a curing catalyst for a sealant or the like. That is, such known aluminum chelate compound may not necessarily be the most appropriate option depending on the intended use.

Meanwhile, as a room temperature fast-curable organopolysiloxane composition of a condensation curing type, there have been known a one-solution type where a rate of crosslinking due to hydrolysis is improved by using a curing agent on a base polymer which is an organopolysiloxane having both terminal ends blocked by hydroxy groups; and a two-solution type where a base polymer which is an organopolysiloxane having both terminal ends blocked by hydroxy groups and a crosslinking agent are packed separately.

There have been known various room temperature-curable compositions that can be cured to form elastomers at room temperatures. Particularly, a type of composition that releases an alcohol(s) when being cured does not generate an unpleasant smell and cause metals to corrode. Therefore, such a type of composition is preferably used in sealing materials, adhesive agents and coating agents for electronic devices.

As such a type of composition, there have been disclosed a composition consisting of a polyorganosiloxane having its terminal ends blocked by hydroxyl groups, an alkoxysilane and an organic titanium compound; a composition consisting of a polyorganosiloxane having its terminal ends blocked by alkoxysilyl groups, an alkoxysilane and an alkoxy titanium; a composition consisting of a linear polyorganosiloxane having its terminal ends blocked by alkoxysilyl groups and including a silethylene group(s), an alkoxysilane and an alkoxy titanium; and a composition consisting of a polyorganosiloxane having its terminal ends blocked by hydroxyl groups or a polyorganosiloxane having its terminal ends blocked by alkoxy groups and an alkoxy-α-silyl ester compound (Patent documents 2 to 5).

Although these compositions are superior in preservation stability, water resistance and moisture resistance, they have exhibited insufficient fast curabilities.

As described above, a polymer having a reactive alkoxysilyl group at its terminal ends is heretofore known. Since this polymer already has its polymer terminal ends blocked by alkoxysilyl groups, there can be obtained a composition exhibiting a superior preservation stability and a curability that does not easily change (deteriorate) with time. Further, a workability (viscosity, thixotropy) thereof can be arbitrarily adjusted; there can be formed a cross-linkage and an elastomer thereof by reaction with the water in the air; and superior properties (hardness, tensile strength, elongation at break) can also be achieved.

However, since an alcohol-type curable composition has a low reactivity with the water in the air as compared to heretofore known curable compositions of other curing types such as an oxime-type, an acetic acid-type and an acetone-type, restrictions are imposed on locations where an alcohol-type curable composition can be used.

In response, studies have been made on a functional group (linking group) adjacent to a reactive alkoxy group, and it has been reported that an a-alkoxysilylmethyl terminal end group is particularly highly reactive with the water in the air (Patent document 6). However, there exist downsides including a still insufficient curability; a negative impact inflicted on durability by the adjacent functional group (linking group); and a low restorability of a cured product.

In addition, by attempting to solve the problem of the curability, there arises another problem where yellowing occurs after performing an anti-UV discoloration test.

PRIOR ART DOCUMENT

Patent Documents

Patent document 1: Japanese Patent No.3850969
Patent document 2: Japanese Examined Patent Application Publication No. Sho 39-27643
Patent document 3: JP-A-Sho 55-43119
Patent document 4: Japanese Examined Patent Application Publication No. Hei 7-39547
Patent document 5: JP-A-Hei 7-331076
Patent document 6: Japanese Unexamined Patent Application Publication (Translation of PCT Application) No.2012-511607
}

SUMMARY OF THE INVENTION

Problem to be Solved by the Invention

The present invention was made in view of the aforementioned issues. It is an object of the invention to provide a novel aluminum chelate compound useful as, for example, a catalyst of a room temperature-curable resin; and a room temperature-curable resin composition capable of forming a cured product not only superior in fast curability, preservation stability and durability, but also superior in UV-discoloration resistance, such room temperature-curable resin composition particularly being a room temperature-curable organopolysiloxane composition.

Means to Solve the Problem

As a result of diligently conducting numerous studies to achieve the abovementioned objectives, the inventors of the present invention found that the aluminum chelate compound shown below was useful in solving the aforementioned problems. Moreover, the inventors found that there could be obtained a room temperature-curable composition capable of forming a cured product superior in fast curability, preservation stability, durability and UV-discoloration resistance by using a polymer and/or compound having an alkoxysilyl-ethylene group(s), where a linking group adjacent to an alkoxysilyl group is an ethylene group; and by using an aluminum chelate compound, particularly the following aluminum chelate compound as a curing catalyst. In this way, the inventors completed the present invention.

That is, the present invention provides the following aluminum chelate compound, room temperature-curable resin composition and the like.

<1> An aluminum chelate compound having a β-dicarbonyl compound represented by the following general formula (1):

[Chemical formula 1]

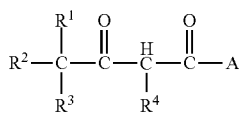

(1)

(wherein each of $R^1$ to $R^3$ represents a halogen atom or a substituted or unsubstituted monovalent hydrocarbon group having 1 to 12 carbon atoms, $R^1$ to $R^3$ being either identical to or different from one another; $R^4$ represents a hydrogen atom or a substituted or unsubstituted monovalent hydrocarbon group having 1 to 12 carbon atoms; and A is a group represented by the following formula (2) or a group represented by —$OR^8$:

Chemical formula 2]

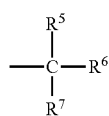

(2)

wherein each of $R^5$ to $R^7$ represents a halogen atom or a substituted or unsubstituted monovalent hydrocarbon group having 1 to 12 carbon atoms, $R^5$ to $R^7$ being either identical to or different from one another; and $R^8$ represents a substituted or unsubstituted monovalent hydrocarbon group having 1 to 5 carbon atoms), provided that an average coordination number of the β-dicarbonyl compound represented by the general formula (1) to aluminum is 0.5 to 2.5.

<2> The aluminum chelate compound according to <1>, having a β-ketoester represented by the following formula (3) and a diketone represented by the following formula (4):

[Chemical formula 3]

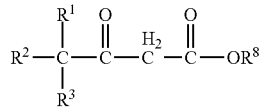

(3)

(wherein each of $R^1$ to $R^3$ represents a halogen atom or a substituted or unsubstituted monovalent hydrocarbon group having 1 to 12 carbon atoms, $R^1$ to $R^3$ being either identical to or different from one another; and $R^8$ represents a substituted or unsubstituted monovalent hydrocarbon group having 1 to 5 carbon atoms)

[Chemical formula 4]

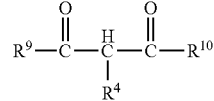

(4)

(wherein each of $R^9$ and $R^{10}$ represents a substituted or unsubstituted monovalent hydrocarbon group having 1 to 12 carbon atoms, $R^9$ and $R^{10}$ being either identical to or different from each other; and $R^4$ represents a hydrogen atom or a substituted or unsubstituted monovalent hydrocarbon group having 1 to 12 carbon atoms), provided that an average molecular coordination number of the β-ketoester represented by the formula (3) to aluminum is 0.5 to 2.5, an average molecular coordination number of the diketone represented by the formula (4) to aluminum is 0.5 to 2.5, and an average molecular coordination number of a total of the formulae (3) and (4) is 3.0.

<3> The aluminum chelate compound according to <1>, having a diketone represented by the following formula (5) and a β-ketoester represented by the following formula (6):

[Chemical formula 5]

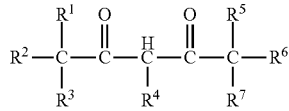

(5)

(wherein each of $R^1$ to $R^3$ represents a halogen atom or a substituted or unsubstituted monovalent hydrocarbon group having 1 to 12 carbon atoms, $R^1$ to $R^3$ being either identical to or different from one another; $R^4$ represents a hydrogen atom or a substituted or unsubstituted monovalent hydrocarbon group having 1 to 12 carbon atoms; and each of $R^5$ to $R^7$ represents a halogen atom or a substituted or unsubstituted monovalent hydrocarbon group having 1 to 12 carbon atoms, $R^5$ to $R^7$ being either identical to or different from one another)

[Chemical formula 6]

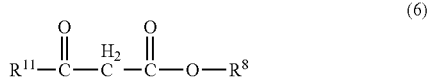

(6)

(wherein $R^{11}$ represents a linear monovalent hydrocarbon group having 1 to 12 carbon atoms; and $R^8$ represents a substituted or unsubstituted monovalent hydrocarbon group having 1 to 5 carbon atoms), provided that an average molecular coordination number of the diketone represented by the formula (5) to aluminum is 0.5 to 2.5, an average molecular coordination number of the β-ketoester represented by the formula (6) to aluminum is 0.5 to 2.5, and an average molecular coordination number of a total of the formulae (5) and (6) is 3.0.

As for the aluminum chelate compounds of the present invention that are defined above, an aggregate of aluminum chelate compounds belongs to the scope of the present invention as long as an average structure thereof as an aluminum chelate compound aggregate belongs to the scope shown above, even when the aluminum chelate compounds differ from one another in structure.

<4> Further, the present invention also provides a curing catalyst of a resin containing the aforementioned aluminum chelate compound.

<5> A room temperature-curable resin composition including:

(A) 100 parts by mass of an alkoxysilyl-ethylene group terminated polymer having in one molecule at least one structure represented by the following general formula:

[Chemical formula 7]

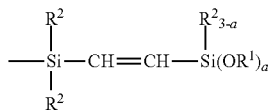

(wherein each of $R^1$ and $R^2$ represents a substituted or unsubstituted monovalent hydrocarbon group having 1 to 12 carbon atoms, $R^1$ and $R^2$ being either identical to or different from each other; and a represents 2 or 3); and (D) 0.001 to 15 parts by mass of an aluminum chelate compound.

<6> A room temperature-curable organopolysiloxane composition including:

(B) 100 parts by mass of a diorganopolysiloxane having in one molecule at least two silicon atoms, each silicon atom being bonded to a hydroxyl group and/or a hydrolyzable group;

(C) 0.1 to 30 parts by mass of an alkoxysilyl-ethylene group-containing compound having in one molecule at least one structure represented by the following general formula:

[Chemical formula 8]

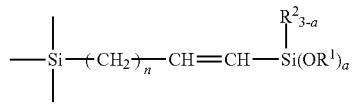

(wherein each of $R^1$ and $R^2$ represents a substituted or unsubstituted monovalent hydrocarbon group having 1 to 12 carbon atoms, $R^1$ and $R^2$ being either identical to or different from each other; a represents 2 or 3; and n represents an integer of 0 to 10); and (D) 0.001 to 15 parts by mass of an aluminum chelate compound.

<7> The room temperature-curable resin composition according to <5> or <6>, wherein the component (D) is the aluminum chelate compound as set forth in <1>, <2> or <3>.

<8> A molded product obtained by curing the room temperature-curable resin composition of any one of <5> to <7>.

<9> A coating, adhesive or sealing agent including the room temperature-curable resin composition of any one of <5> to <7>.

Effects of the Invention

The novel aluminum chelate compound of the present invention exhibits a superior catalyst activity when used as a curing catalyst of a resin. This aluminum chelate compound is particularly useful as a curing catalyst of a room temperature-curable resin.

Further, the room temperature-curable organopolysiloxane composition of the present invention is not only superior in heat resistance, water resistance and moisture resistance, but also superior in fast curability and preservation stability. Particularly, this room temperature-curable organopolysiloxane composition is capable of forming a cured product exhibiting a small degree of UV discoloration. For example, the composition of the present invention can be immediately cured when exposed to the air, even after being stored for 12 months. Moreover, since there is no need to use a tin compound which is subject to control in recent years, the composition of the present invention bears a low environmental burden.

Therefore, the room temperature-curable organopolysiloxane composition of the present invention is useful as a sealing material, a coating agent and an adhesive agent that are applied in locations requiring a heat resistance, a water resistance and a moisture resistance. Particularly, this room temperature-curable organopolysiloxane composition is useful as an adhesive agent for architecture purpose; and electrical and electronic purpose, where a steam resistance and water resistance are required.

MODE FOR CARRYING OUT THE INVENTION

<Aluminum Chelate Compound>

Figure 1:
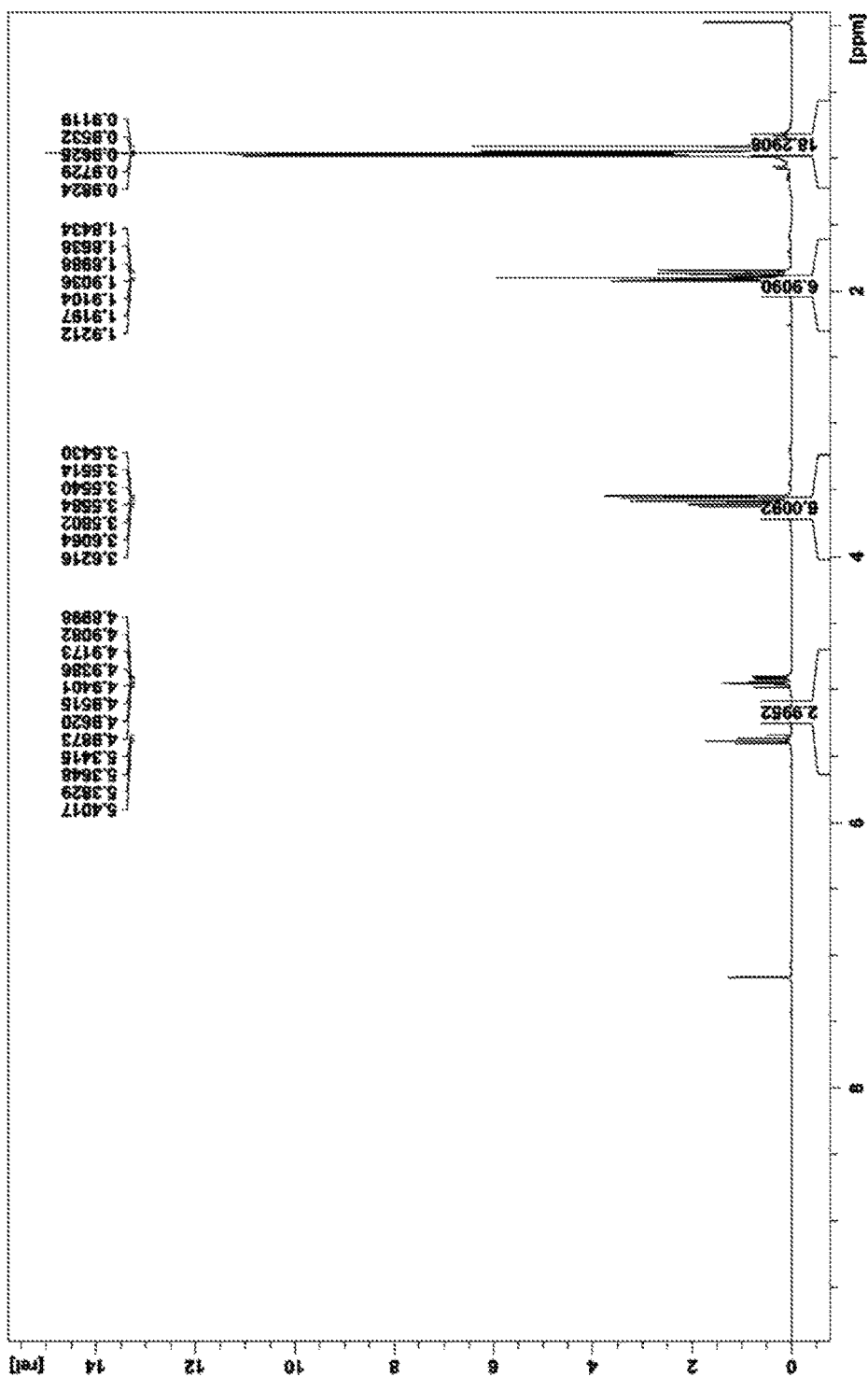
FIG. 1 is a $^1$HNMR chart of an aluminum chelate compound obtained in a first working example.

The aforementioned aluminum chelate compound of the present invention is a compound suitable as a curing agent of a room temperature-curable resin.

Here, in the above general formulas (1) and (2), substituted or unsubstituted monovalent hydrocarbon groups each having 1 to 12 carbon atoms, which are represented by $R^1$ to $R^7$, can be either linear, cyclic or branched. Examples of such monovalent hydrocarbon group include a linear alkyl group such as a methyl group, an ethyl group, a propyl group, an n-butyl group, a hexyl group, a heptyl group, an octyl group, a nonyl group and a decyl group; a cyclic alkyl group such as a cyclohexyl group; a branched alkyl group such as an t-butyl group and a 2-ethylhexyl group; and a substituted group e.g. a halogen-substituted monovalent hydrocarbon group such as a trifluoromethyl group, a bromoethyl group and a trichloropropyl group that are obtained by substituting a part or all of the hydrogen atoms of the aforementioned linear, cyclic or branched alkyl groups with a halogen atom(s) such as a chlorine, a fluorine and a bromine atom(s). Examples of such halogen atoms include chlorine, fluorine and bromine atoms. These groups may be either identical to or different from one another. It is preferred that each of $R^1$ to $R^3$ and $R^5$ to $R^8$ of the present invention be a methyl group, an ethyl group or a fluorine atom. Particularly, it is preferred that $R^4$ be either a hydrogen atom or a methyl group.

Here, in the above general formula (3), substituted or unsubstituted monovalent hydrocarbon groups each having 1 to 12 carbon atoms, which are represented by $R^1$ to $R^3$, can be either linear, cyclic or branched. Examples of such monovalent hydrocarbon group include a linear alkyl group such as a methyl group, an ethyl group, a propyl group, an n-butyl group, a hexyl group, a heptyl group, an octyl group, a nonyl group and a decyl group; a cyclic alkyl group such as a cyclohexyl group; a branched alkyl group such as an t-butyl group and a 2-ethylhexyl group; and a substituted group e.g. a halogen-substituted monovalent hydrocarbon group such as a trifluoromethyl group, a bromoethyl group and a trichloropropyl group that are obtained by substituting a part or all of the hydrogen atoms of the aforementioned linear, cyclic or branched alkyl groups with a halogen atom(s) such as a chlorine, a fluorine and a bromine atom(s). Examples of such halogen atoms include chlorine, fluorine and bromine atoms. These groups may be either identical to or different from one another. A substituted or unsubstituted monovalent hydrocarbon group having 1 to 5 carbon atoms, which is represented by $R^8$, can be either linear, cyclic or branched. Examples of this monovalent hydrocarbon group include a linear alkyl group such as a methyl group, an ethyl group, a propyl group and an n-butyl group; a cyclic alkyl group such as a cyclopentyl group; a branched alkyl group such as a t-butyl group; and a substituted group e.g. a halogen-substituted monovalent hydrocarbon group such as a trifluoromethyl group, a bromoethyl group and a trichloropropyl group that are obtained by substituting a part or all of the hydrogen atoms of the aforementioned linear, cyclic or branched alkyl groups with a halogen atom(s) such as a chlorine, a fluorine and a bromine atom(s). It is preferred that each of $R^1$ to $R^3$ of the present invention be a methyl group and/or a fluorine atom. Particularly, it is preferred that $R^8$ be a methyl group and/or an ethyl group.

Here, in the above general formula (4), substituted or unsubstituted monovalent hydrocarbon groups each having 1 to 12 carbon atoms, which are represented by $R^4$, $R^9$ and $R^{10}$, can be either linear, cyclic or branched. Examples of such monovalent hydrocarbon group include a linear alkyl group such as a methyl group, an ethyl group, a propyl group, an n-butyl group, a hexyl group, a heptyl group, an octyl group, a nonyl group and a decyl group; a cyclic alkyl group such as a cyclohexyl group; a branched alkyl group such as a t-butyl group and a 2-ethylhexyl group; and a substituted group e.g. a halogen-substituted monovalent hydrocarbon group such as a trifluoromethyl group, a bromoethyl group and a trichloropropyl group that are obtained by substituting a part or all of the hydrogen atoms of the aforementioned linear, cyclic or branched alkyl groups with a halogen atom(s) such as a chlorine, a fluorine and a bromine atom(s). These groups may be either identical to or different from one another. It is preferred that $R^9$ and $R^{10}$ of the present invention be a methyl group and/or an ethyl group. Particularly, it is preferred that $R^4$ be a hydrogen atom and/or a methyl group.

Here, in the above general formula (5), substituted or unsubstituted monovalent hydrocarbon groups each having 1 to 12 carbon atoms, which are represented by $R^1$ to $R^7$, can be either linear, cyclic or branched. Examples of such monovalent hydrocarbon group include a linear alkyl group such as a methyl group, an ethyl group, a propyl group, an n-butyl group, a hexyl group, a heptyl group, an octyl group, a nonyl group and a decyl group; a cyclic alkyl group such as a cyclohexyl group; a branched alkyl group such as a t-butyl group and a 2-ethylhexyl group; and a substituted group e.g. a halogen-substituted monovalent hydrocarbon group such as a trifluoromethyl group, a bromoethyl group and a trichloropropyl group that are obtained by substituting a part or all of the hydrogen atoms of the aforementioned linear, cyclic or branched alkyl groups with a halogen atom(s) such as a chlorine, a fluorine and a bromine atom(s). These groups may be either identical to or different from one another. It is preferred that each of $R^1$ to $R^3$ and $R^5$ to $R^7$ of the present invention be a methyl group and/or an ethyl group. Particularly, it is preferred that $R^4$ be a hydrogen atom and/or a methyl group.

Here, in the above general formula (6), an unsubstituted monovalent linear hydrocarbon group having 1 to 12 carbon atoms, which is represented by $R^{11}$, can be, for example, a linear alkyl group such as a methyl group, an ethyl group, a propyl group, an n-butyl group, a hexyl group, a heptyl group, an octyl group, a nonyl group and a decyl group. A substituted or unsubstituted monovalent hydrocarbon group having 1 to 5 carbon atoms, which is represented by $R^8$, can be either linear, cyclic or branched. Examples of such monovalent hydrocarbon group include a linear alkyl group such as a methyl group, an ethyl group, a propyl group and an n-butyl group; a cyclic alkyl group such as a cyclopentyl group; a branched alkyl group such as a t-butyl group; and a substituted group e.g. a halogen-substituted monovalent hydrocarbon group such as a trifluoromethyl group, a bromoethyl group and a trichloropropyl group that are obtained by substituting a part or all of the hydrogen atoms of the aforementioned linear, cyclic or branched alkyl groups with a halogen atom(s) such as a chlorine, a fluorine and a bromine atom(s). It is preferred that $R^{11}$ of the present invention be a methyl group and/or an ethyl group. Particularly, it is preferred that $R^8$ be a methyl group and/or an ethyl group.

The aluminum chelate derivative of the present invention can, for example, be produced through the following method. That is, aluminum alkoxide is to be dissolved in an appropriate solvent such as toluene, followed by delivering β-ketoester and then β-diketone by drops into such solution before stirring the same at a room temperature. Later, by removing the solvent and/or alcohol from such reaction solution, there can be produced the target aluminum chelate compound.

<Room Temperature-Curable Resin Composition>
[Component (A)]

In the present invention, a component (A) is an alkoxysilyl-ethylene group terminated polymer having at least one structure represented by the following general formula in one molecule

[Chemical formula 9]

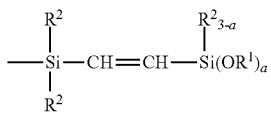

(in the above formula, each of $R^1$ and $R^2$ is a substituted or unsubstituted monovalent hydrocarbon group having 1 to 12 carbon atoms. $R^1$ and $R^2$ may be identical to or different from each other, and a represents either 2 or 3.)

In the above formula, examples of the substituted or unsubstituted monovalent hydrocarbon group represented by $R^1$ and $R^2$ include an alkyl group such as a methyl group, an ethyl group, a propyl group, a butyl group, a pentyl group, a hexyl group, a heptyl group, an octyl group, a nonyl group, a decyl group and an octadecyl group; a cycloalkyl group such as a cyclopentyl group and a cyclohexyl group; an alkenyl group such as a vinyl group, an allyl group, a butenyl group, a pentenyl group and a hexenyl group; an aryl group such as a phenyl group, a tolyl group, a xylyl group and an α-naphthyl group, β-naphthyl group; an aralkyl group such as a benzyl group, a 2-phenylethyl group and a 3-phenylpropyl group; and substituted groups obtained by substituting a part or all of the hydrogen atoms of any of the abovementioned groups with halogen atoms such as F, Cl and Br or with cyano groups or the like, such substituted groups including a 3-chloropropyl group, a 3,3,3-trifluoropropyl group, a 2-cyanoethyl group and the like. Among these groups, a methyl group and an ethyl group are preferred, and a methyl group is particularly preferred.

Examples of a hydrolyzable group ($R^1O$—) at the terminal end(s) of a molecular chain include an alkoxy group such as a methoxy group, an ethoxy group, a propoxy group and a 2-ethylhexoxy group; and an alkoxyalkoxy group such as a methoxyethoxy group, an ethoxyethoxy group and a methoxypropoxy group. Among these groups, a methoxy group and an ethoxy group are particularly preferred because of their fast curabilities.

The component (A) is used as a main agent (base polymer) of the composition, and may be either linear or branched. The aforementioned polymer may be composed of various units such as polysiloxane, polyether, polyurethane, polyurea, polyester, polysiloxane-urea/urethane copolymer, polyacrylate, polymethacrylate, polycarbonate, polystyrene, polyamide, polyvinyl ester, polyolefin, polyethylene, polybutadiene, ethylene-olefin copolymer, and styrene-butadiene copolymer. An arbitrary mixture or combination of these polymers can also be used.

Especially, a polysiloxane having an alkoxysilyl-ethylene group at its terminal end(s) is a novel compound that is superior in durability and can be used favorably. Specific examples of such polysiloxane include the diorganopolysiloxane represented by the following general formulas (12) and/or (13).

[Chemical formula 10]

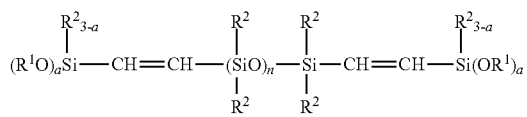

(12)

[Chemical formula 11]

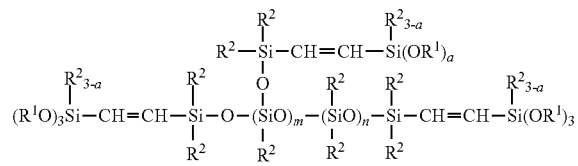

(13)

(in the above formulas, each of $R^1$ and $R^2$ represents a substituted or unsubstituted monovalent hydrocarbon group having 1 to 12 carbon atoms; a represents 2 or 3; m represents an integer of 1 to 10; n represents a number by which the diorganopolysiloxane exhibits a viscosity of 10 to 1,000,000 mPa·s at 25° C.)

In the above formulas, examples of the substituted or unsubstituted monovalent hydrocarbon group having 1 to 12 carbon atoms, which is represented by $R^1$ and $R^2$, include an alkyl group such as a methyl group, an ethyl group, a propyl group, a butyl group, a pentyl group, a hexyl group, a heptyl group, an octyl group, a nonyl group, a decyl group and an octadecyl group; a cycloalkyl group such as a cyclopentyl group and a cyclohexyl group; an alkenyl group such as a vinyl group, an allyl group, a butenyl group, a pentenyl group and a hexenyl group; an aryl group such as a phenyl group, a tolyl group, a xylyl group and an α-, β-naphthyl group; an aralkyl group such as a benzyl group, a 2-phenylethyl group and a 3-phenylpropyl group; and substituted groups obtained by substituting a part or all of the hydrogen atoms of any of the abovementioned groups with halogen atoms such as F, Cl and Br or with cyano groups or the like, such substituted groups including a 3-chloropropyl group, a 3,3,3-trifluoropropyl group, a 2-cyanoethyl group and the like. Among these groups, a methyl group and an ethyl group are preferred, and a methyl group is particularly preferred.

Examples of a hydrolyzable group ($R^1O$—) at the terminal end(s) of a molecular chain include an alkoxy group such as a methoxy group, an ethoxy group, a propoxy group and a 2-ethylhexoxy group; and an alkoxyalkoxy group such as a methoxyethoxy group, an ethoxyethoxy group and a methoxypropoxy group. Among these groups, a methoxy group and an ethoxy group are particularly preferred because of their fast curabilities.

At the temperature of 25° C., it is preferred that the polymer as the component (A) exhibit a viscosity of 10 to 1,000,000 mPa·s, more preferably 50 to 500,000 mPa·s, particularly preferably 100 to 100,000 mPa·s, especially preferably 100 to 80,000 mPa·s. It is preferable when the viscosity of the diorganopolysiloxane is not lower than 10 mPa·s, because there can be easily obtained a coating film superior in physical and mechanical strengths in such case. It is also preferable when such viscosity is not higher than 1,000,000 mPa·s, because the viscosity of the composition will not be become excessively high in such case so that a favorable workability can be achieved at the point of use. Here, the viscosity refers to a value measured by a rotary viscometer.

The polymer as the component (A) can be produced as follows. For example, a diorganopolysiloxane having ethynyl groups at both of its terminal ends is first produced by a polymerization reaction between a disiloxane having acetylene groups at both of its terminal ends and an octamethylcyclotetrasiloxane under the presence of a sulfuric acid. Next, a trialkoxysilane is added thereto to obtain the polymer as the component (A).

As a catalyst for addition reaction used here, there can be employed a platinum group metal based catalyst such as a platinum based catalyst, a palladium based catalyst and a rhodium based catalyst, among which a platinum based catalyst is particularly preferred. Examples of such platinum based catalyst include catalysts with a solid platinum being supported on a support such as platinum black, alumina or silica; a chloroplatinic acid; an alcohol-modified chloroplatinic acid; a complex of a chloroplatinic acid and olefin; or a complex of platinum and vinyl siloxane. The amount of these catalysts used may be a so-called catalytic amount. These catalysts can be used in an amount of 0.1 to 1,000 ppm, particularly 0.5 to 100 ppm with respect to, for example, trialkoxysilanes, in terms of platinum group metal.

It is desired that this reaction be normally performed at a temperature of 50 to 120° C., particularly 60 to 100° C., for 0.5 to 12 hours, particularly 1 to 6 hours. Further, although this reaction may be performed without using a solvent, there can be employed an appropriate solvent such as toluene and xylene if necessary, provided that there will be no adverse impact on the aforementioned addition reaction or the like.

In an addition reaction to an acetylene group(s), a geometric isomer represented by the following formula (14) is formed. Trans-isomers are richly produced and highly reactive in the geometric isomers. And, it is not required that trans-isomers and cis-isomers be separated when using the diorganopolysiloxane of the present invention because of no adverse impact on the properties of the diorganopolysiloxane.

[Chemical formula 12]

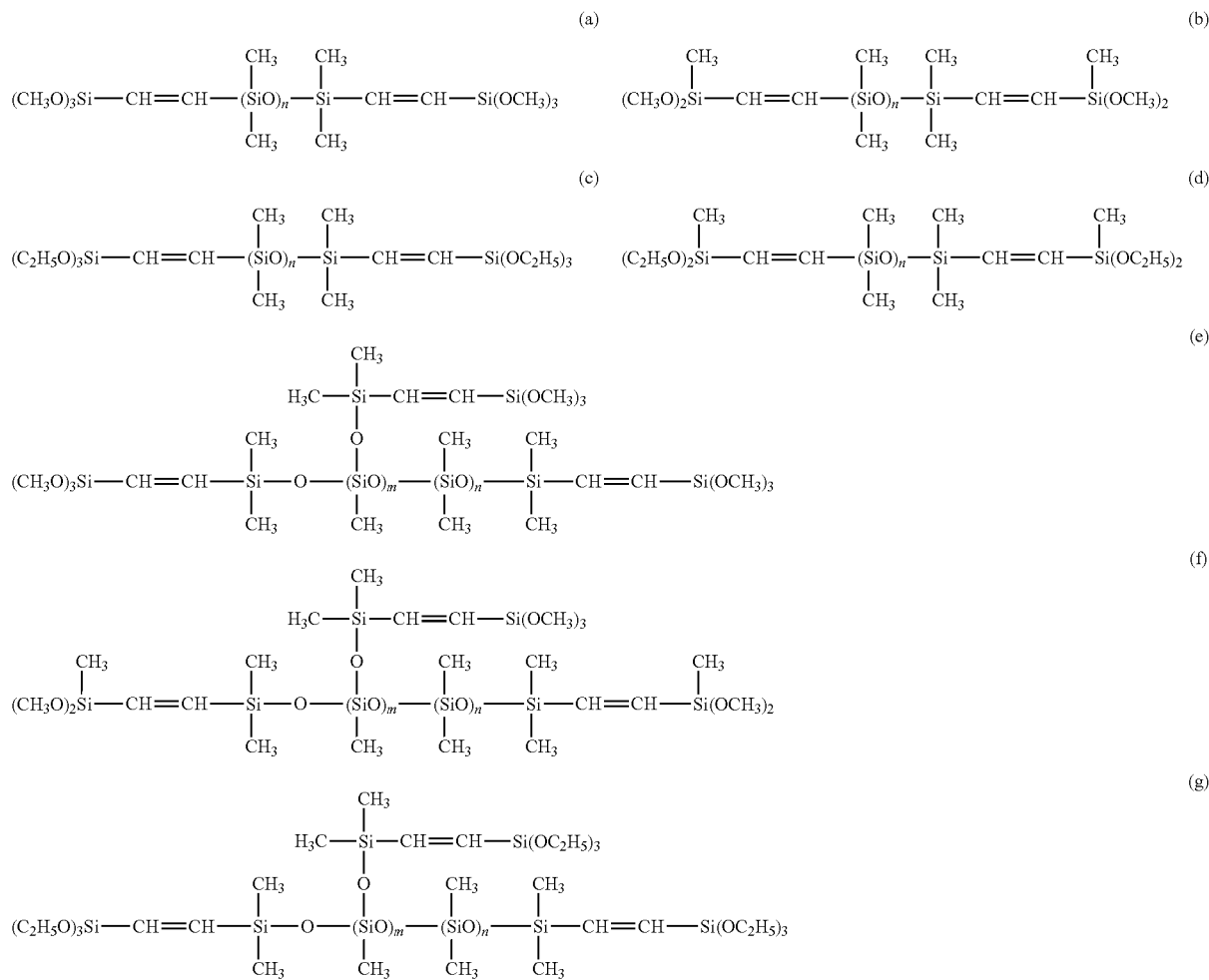

Specific examples of the diorganopolysiloxane as the component (A) are as follows.

[Chemical formula 13]

(in the above formulas, the definitions of m, n, $R^1$ and $R^2$ are identical to those of the component (A).)

As for the diorganopolysiloxane as the component (A), there may be used either one kind thereof; or not less than two kinds thereof with differing structures and molecular weights.

[Component (B)]

A diorganopolysiloxane as a component (B) is a main agent (base polymer) of the room temperature-curable organopolysiloxane composition of the present invention. The diorganopolysiloxane as the component (B) has at least two hydroxyl groups or hydrolyzable groups that are bonded to silicone atoms, in each molecule. Specific examples of such diorganopolysiloxane include the following diorganopolysiloxanes with the terminal ends of their molecular chains being blocked by hydroxyl groups or hydrolyzable groups, as represented by the general formulas (15) and (16) below.

[Chemical formula 14]

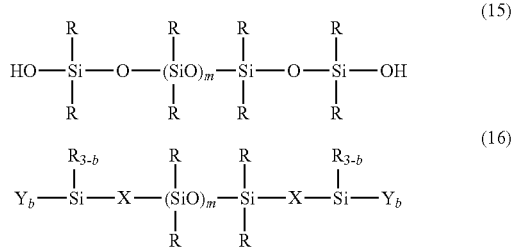

(in the above formula, R represents a substituted or unsubstituted monovalent hydrocarbon group having 1 to 12, preferably 1 to 8 carbon atoms; X represents a bivalent hydrocarbon group having 1 to 8, preferably 1 to 6 oxygen or carbon atoms; Y represents a hydrolyzable group; b represents 2 or 3; m represents a number by which this diorganopolysiloxane exhibits a viscosity of 100 to 1,000,000 mPa·s at 25° C.)

In the above formula, examples of the substituted or unsubstituted monovalent hydrocarbon group represented by R include an alkyl group such as a methyl group, an ethyl group, a propyl group, a butyl group, a pentyl group, an hexyl group, a heptyl group, an octyl group, a nonyl group, a decyl group and an octadecyl group; a cycloalkyl group such as a cyclopentyl group and a cyclohexyl group; an alkenyl group such as a vinyl group, an allyl group, a butenyl group, a pentenyl group and a hexenyl group; an aryl group such as a phenyl group, a tolyl group, a xylyl group and an α-naphthyl group, β-naphthyl group; an aralkyl group such as a benzyl group, a 2-phenylethyl group and a 3-phenylpropyl group; and substituted groups obtained by substituting a part or all of the hydrogen atoms of any of the abovementioned groups with halogen atoms such as F, Cl and Br or with cyano groups or the like, such substituted groups including a 3-chloropropyl group, a 3,3,3-trifluoropropyl group, a 2-cyanoethyl group and the like. Among these groups, a methyl group, an ethyl group and a phenyl group are preferred, and a methyl group is particularly preferred.

X represents a bivalent hydrocarbon group having 1 to 8 oxygen or carbon atoms. It is preferred that X as a bivalent hydrocarbon group be represented by —$(CH_2)_p$— (p represents an integer of 1 to 8), among which an oxygen atom and —$CH_2CH_2$— are preferred.

Y represents a hydrolyzable group at the terminal ends of the molecular chain of the aforementioned diorganopolysiloxane. Examples of such hydrolyzable group include an alkoxy group such as a methoxy group, an ethoxy group and a propoxy group; an alkoxyalkoxy group such as a methoxyethoxy group, an ethoxyethoxy group and a methoxypropoxy group; an acyloxy group such as an acetoxy group, an octanoyloxy group and a benzoyloxy group; an alkenyloxy group such as a vinyloxy group, an isopropenyloxy group and a 1-ethyl-2-methylvinyloxy group; a ketoxime group such as a dimethylketoxime group, an methylethyl ketoxime group and a diethylketoxime group; an amino group such as a dimethylamino group, a diethylamino group, a butylamino group and a cyclohexylamino group; an aminoxy group such as a dimethylaminoxy group and a diethylaminoxy group; and an amide group such as an N-methylacetamide group, an N-ethylacetamide group and an N-methylbenzamide group. Among these groups, an alkoxy group is preferred, a methoxy group and an ethoxy group are more preferred, and a methoxy group is particularly preferred.

At the temperature of 25° C., it is preferred that the diorganopolysiloxane as the component (B) exhibit a viscosity of 100 to 1,000,000 mPa·s, more preferably 300 to 500,000 mPa·s, particularly preferably 500 to 100,000 mPa·s, especially 1,000 to 80,000 mPa·s. When the viscosity of such diorganopolysiloxane is lower than 100 mPa·s, it may be difficult to obtain a cured product superior in physical and mechanical strengths. A viscosity greater than 1,000,000 mPa·s leads to an excessively high viscosity of the composition such that an unfavorable workability will be resulted at the point of use. Here, such viscosity is a value measured by a rotary viscometer.

Specific examples of the diorganopolysiloxane as the component (B) include those represented by the following formulas.

[Chemical formula 15]

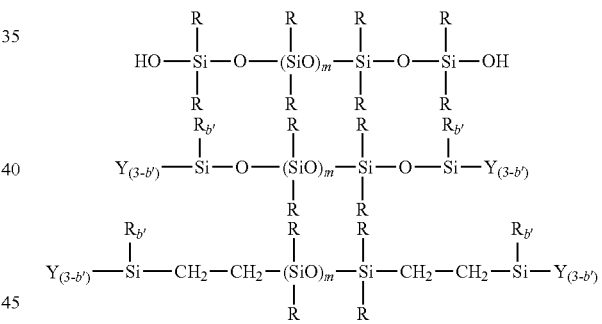

(in the above formulas, the definitions of m, R and Y are identical to those of the component (B); b' represents 0 or 1.)

As for the diorganopolysiloxane as the component (B), there may be used either one kind thereof; or not less than two kinds thereof with differing structures and degrees of polymerization.

[Component (C)]

A component (C) is an alkoxysilyl-ethylene group-containing compound having at least one structure represented by the following formula in one molecule. The component (C) serves as a cross-linking agent of the component (B).

[Chemcial formula 16]

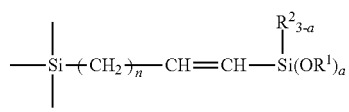

(in the above formula, each of $R^1$ and $R^2$ represents a substituted or unsubstituted monovalent hydrocarbon group having 1 to 12 carbon atoms; $R^1$ and $R^2$ may be identical to or different from each other; a represents 2 or 3; n represents an integer of 0 to 10.)

A compound having the aforementioned structure can, for example, be obtained by adding a silane having an acetylene group(s) and a trialkoxysilane.

As a catalyst for addition reaction used here, there can be employed a platinum group metal based catalyst such as a platinum based catalyst, a palladium based catalyst and a rhodium based catalyst, among which a platinum based catalyst is particularly preferred. Examples of such platinum based catalyst include catalysts with a solid platinum being supported on a support such as platinum black, alumina or silica; a chloroplatinic acid; an alcohol-modified chloroplatinic acid; a complex of a chloroplatinic acid and olefin; or a complex of platinum and vinyl siloxane. The amount of these catalysts used may be a so-called catalytic amount. These catalysts can be used in an amount of 0.1 to 1,000 ppm, particularly 0.5 to 100 ppm with respect to, for example, trialkoxysilanes, in terms of platinum group metal.

It is desired that this reaction be normally performed at a temperature of 50 to 120° C., particularly 60 to 100° C., for 0.5 to 12 hours, particularly 1 to 6 hours. Further, although this reaction may be performed without using a solvent, there can be employed an appropriate solvent such as toluene and xylene if necessary, provided that there will be no adverse impact on the aforementioned addition reaction or the like.

In an addition reaction to an acetylene group(s), a geometric isomer represented by the following formula is formed. Because trans-isomers are richly produced and highly reactive in the geometric isomers, it is preferable that the component (C) of the present invention containing the trans-isomer is used.

[Chemical formation 17]

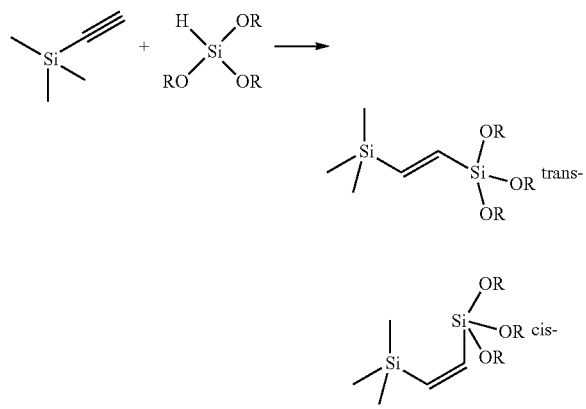

It is preferred that the component (C) such as those described above be added in an amount of 0.1 to 30 parts by mass, particularly 0.5 to 20 parts by mass with respect to 100 parts by mass of the organopolysiloxane as the component (B).

Specific examples of the component (C) include those represented by the following formulas.

[Chemical formula 18]

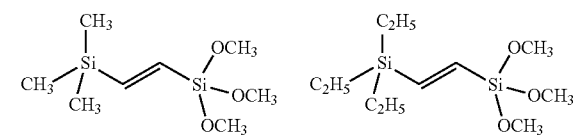

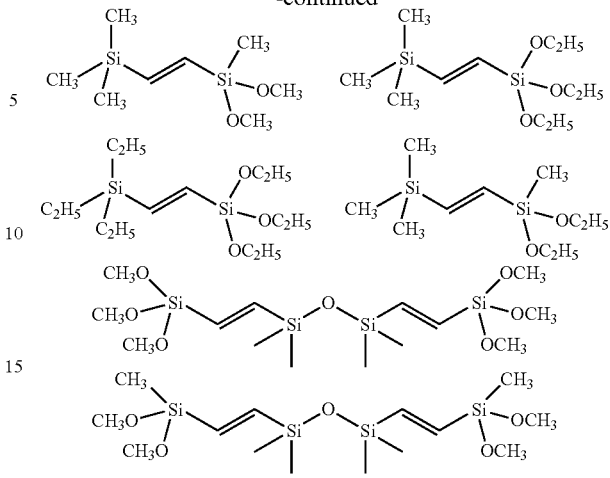

[Component (D)]

An aluminum chelate compound as a component (D) is a curing catalyst and a critical component for obtaining the invention of the present application. Examples of the aluminum chelate compound as the component (D) include those described above.

As for such aluminum chelate compound as the component (D), there may be used either one kind thereof; or not less than two kinds thereof in a mixed manner.

It is preferred that the component (D) be added in an amount of 0.001 to 15 parts by mass, particularly 0.005 to 10 parts by mass with respect to 100 parts by mass of the component (A) or the component (B).

As for the room temperature curable-organopolysiloxane composition of the present invention, the following optional components may be added thereto.

[Component (E)]

A component (E) is a silane and/or its partial hydrolysis condensation, serving as a cross-linking agent other than the component (C). Specific examples of such component (E) include ethyl silicate, propyl silicate, methyltrimethoxysilane, methyltriethoxysilane, vinyltrimethoxysilane, vinyltriethoxysilane, methyltris (methoxyethoxy) silane, vinyltris (methoxyethoxy) silane and methyltripropenoxysilane; as well as partial hydrolysis condensation thereof. Not only one kind, but two or more kinds of such compositions can be used in combination.

The component (E) is normally added in an amount of 0 to 30 parts by mass with respect to 100 parts by mass of the component (A) or the component (B). However, it is preferred that the component (E) be added in an amount of 0.1 to 20 parts by mass, more preferably 0.5 to 15 parts by mass with respect to 100 parts by mass of the component (A) or the component (B). When the amount of the component (E) added is greater than 30 parts by mass, there occurs a problem where the cured product hardens in an excessive manner such that an economic disadvantage is resulted.

[Component (F)]

A component (F) is a filler and is used to endow the cured product formed of such composition with a sufficient mechanical strength. While known materials can be used as such filler, examples of this filler include a metal oxide such as a fine powder silica, an aerosol silica, a silica aerogel, a precipitated silica, a diatom earth, an iron oxide, a zinc oxide and a titanium oxide; any of these metal oxides surface-treated with silane; a metal carbonate such as a calcium carbonate, a magnesium carbonate and a zinc carbonate; asbestos; a glass wool; carbon black; a fine powder mica; a molten silica powder; and a synthesized resin powder such as that of polystyrene, polyvinyl chloride or polypropylene.

The component (F) is added in an amount of 0 to 1,000 parts by mass with respect to 100 parts by mass of the component (A) or the component (B). Particularly, it is preferred that the component (F) be added in an amount of 1 to 400 parts by mass with respect to 100 parts by mass of the component (A) or the component (B). When the amount of the component (F) added is greater than 1,000 parts by mass, not only the workability will be impaired due to an increased viscosity of the composition, but it will also be difficult to achieve a rubber elasticity as a rubber strength decreases after curing. When the component (F) is added in an amount of not smaller than 1 part by mass, the mechanical strength of the cured product obtained can be improved sufficiently.

[Component (G)]

A component (G) is an adhesion aid and is used to endow the cured product made from this composition with a sufficient adhesiveness.

As such component (G), particularly preferred are aminosilanes such as γ-aminopropyltriethoxysilane and 3-2-(aminoethylamino) propyltrimethoxysilane; epoxysilanes such as γ-glycidoxypropyltrimethoxysilane and β-(3,4-epoxycyclohexyl) ethyltrimethoxysilane; isocyanate silane and the like.

It is preferred that the component (G) be added in an amount of 0 to 30 parts by mass, particularly 0.1 to 20 parts by mass with respect to 100 parts by mass of the components (A) and (B).

Further, heretofore known additives may be added to the room temperature-curable organopolysiloxane composition of the present invention. Examples of such additives include a pigment; a dye; an anti-aging agent; an antioxidant; an antistatic agent; and a flame retardant such as antimony oxide and chlorinated paraffin. Furthermore, as a thixotropy improver, there can be added a polyether, a fungicide or an antimicrobial agent.

In fact, the room temperature-curable organopolysiloxane composition of the present invention can be obtained by uniformly mixing together the aforementioned components and the aforementioned various additives by a particular amount(s) in a dry atmosphere.

Here, the room temperature-curable organopolysiloxane composition can be cured when left at a room temperature. However, as for a forming method as well as a curing condition(s) thereof, there may be employed heretofore known methods and conditions in accordance with the types of the compositions.

The room temperature-curable organopolysiloxane composition of the present invention thus obtained can be rapidly cured at a room temperature by moisture in the air, thereby forming a rubber elastic body cured product superior in heat resistance, weather resistance, low-temperature property and adhesiveness to various base materials, especially metals. Further, this composition is particularly superior in preservation stability and curability. For example, the composition is capable of being rapidly cured when exposed to the air even after being stored for 6 months, thus forming a cured product having the abovementioned superior properties. Particularly, no toxic or corrosive gas will be emitted at the time of curing such that no rust will occur on a surface treated with such composition. More particularly, since this composition does not cause contact faults among electric/electronic parts, not only it is useful as an insulating material for electric/electronic parts or as an adhesive agent, but the composition may also be widely used as a sealing agent, a coating agent, a covering agent, a mold-releasing treating agent or even a textile treating agent for various base materials. Further, this composition can be cured and formed into various molded products that are superior in heat resistance, weather resistance and the like.

Working Example

Next, working and comparative examples are shown to describe the present invention in detail. However, the present invention is not limited to the following working examples.

Working Example 1

Aluminum triethoxide of 0.81 g (5.0 mmol) and toluene of 2.0 ml were placed in a 50 ml eggplant-shaped flask, followed by delivering thereinto 1.58 g (10.0 mmol) of 4,4-dimethyl-3-oxopentanoic acid methyl and then 0.50 g (5.0 mmol) of 2,4-pentanedione by drops while performing stirring. After performing stirring under a room temperature for 24 hours, the ethanol generated was then distilled to obtain 2.20 g (yield 100%) of a yellow viscous fluid having an average structure of that of a monoacetylacetonate aluminum bis (methylpivaloylacetoacetate) chelate.

A measurement through $^1$H-NMR spectrum was performed (FIG. 1) to confirm the average structure of the product generated.

$^1$H-NMR spectrum:
δ 0.91 to 0.98 ppm (ratio of H: 18, —C(O)—C(CH$_3$)$_3$)
1.84 to 1.92 ppm (ratio of H: 6, —C(O)—CH$_3$)
3.54 to 3.62 ppm (ratio of H: 6, —OCH$_3$)
4.90 to 5.40 ppm (ratio of H: 3, —C(O)CHC(O)—)

According to the results of the measurement through $^1$H-NMR spectrum, it is regarded that the product obtained has the average structure of a monoacetylacetonate aluminum bis (methylpivaloylacetoacetate) chelate represented by the structure of the formula (7).

[Chemical formula 19]

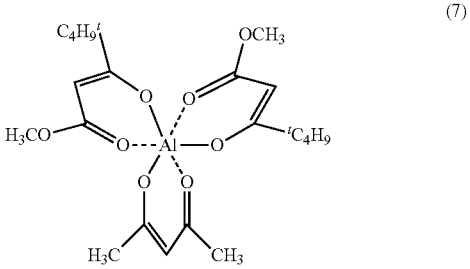

(7)

Working Example 2

Aluminum triethoxide of 0.81 g (5.0 mmol) and toluene of 2.0 ml were placed in a 50 ml eggplant-shaped flask, followed by delivering thereinto 1.84 g (10.0 mmol) of 4,4,4-ethyl trifluoroacetoacetate and then 0.50 g (5.0 mmol) of 2,4-pentanedione by drops while performing stirring. After performing stirring under a room temperature for 24 hours, the ethanol generated was then distilled to obtain 2.46 g (yield 100%) of a yellow viscous fluid having an average structure of that of a monoacetylacetonate aluminum bis (ethyl-4,4,4-trifluoroacetoacetate) chelate.

Figure 2:
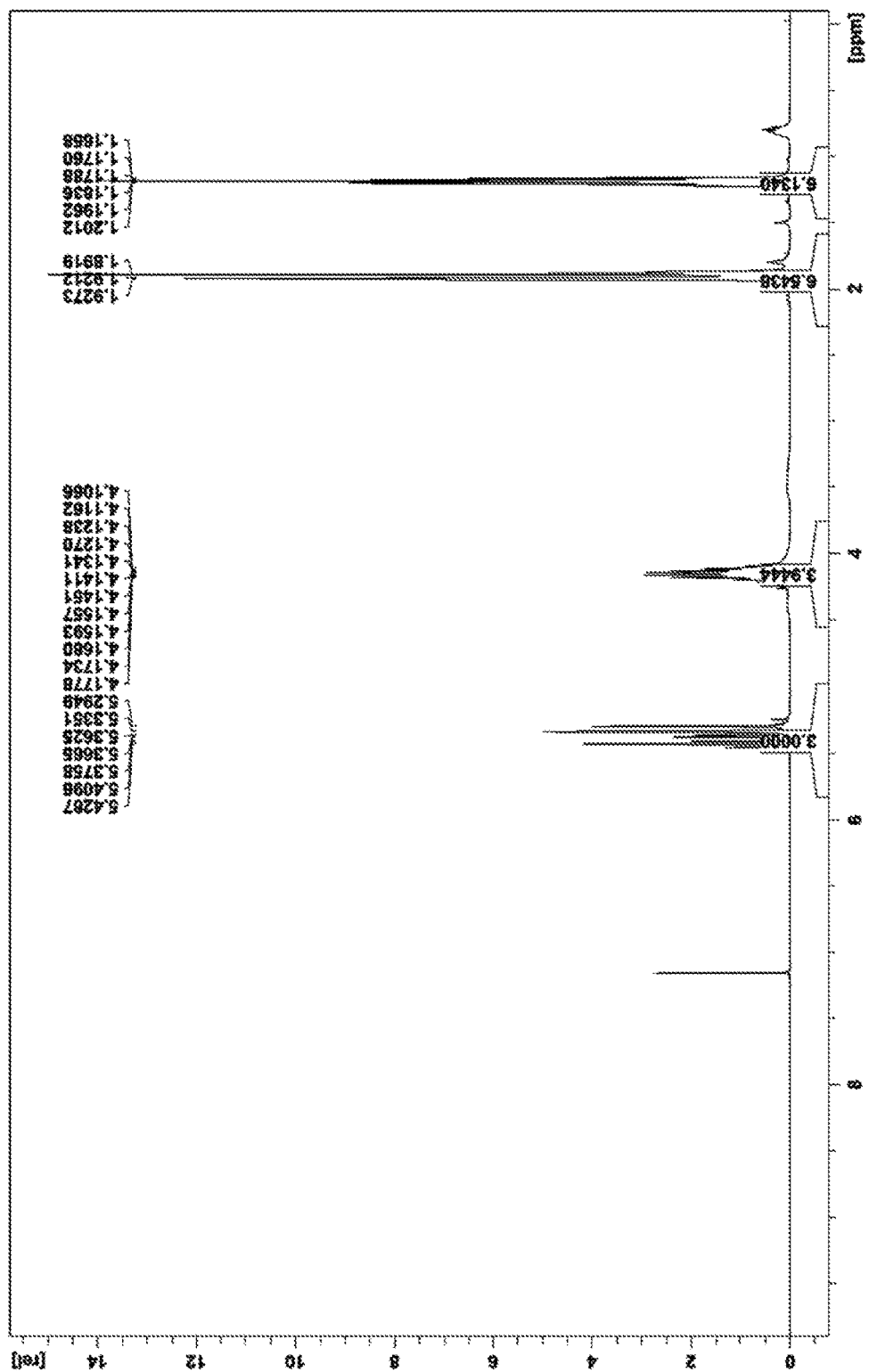
FIG. 2 is a $^1$HNMR chart of an aluminum chelate compound obtained in a second working example.

A measurement through $^1$H-NMR spectrum was performed (FIG. 2) to confirm the average structure of the product generated.

¹H-NMR spectrum:
  δ 1.17 to 1.21 ppm (ratio of H: 6, —OCH₂CH₃)
  1.89 to 1.93 ppm (ratio of H: 6, —C(O)—CH₃)
  4.11 to 4.18 ppm (ratio of H: 4, —OCH₂CH₃)
  5.29 to 5.43 ppm (ratio of H: 3, —C(O)CHC(O)—)

According to the results of the measurement through ¹H-NMR spectrum, it is regarded that the product obtained has the average structure of a monoacetylacetonate aluminum bis (ethyl-4,4,4-trifluoroacetoacetate) chelate represented by the structure of the formula (8).

[Chemical formula 20]

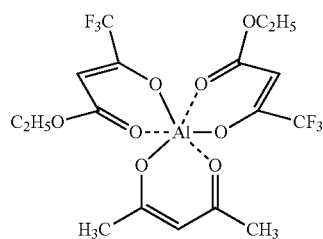

(8)

Working Example 3

Aluminum triethoxide of 0.81 g (5.0 mmol) and toluene of 2.0 ml were placed in a 50 ml eggplant-shaped flask, followed by delivering thereinto 1.30 g (10.0 mmol) of ethyl acetoacetate and then 0.92 g (5.0 mmol) of dipivaloylmethane by drops while performing stirring. After performing stirring under a room temperature for 24 hours, the ethanol and toluene generated were then distilled to obtain 2.34 g (yield 100%) of a yellow viscous fluid having an average structure of that of a mono (dipivaloylmethane) aluminum bis (ethylacetoacetate) chelate.

Figure 3:
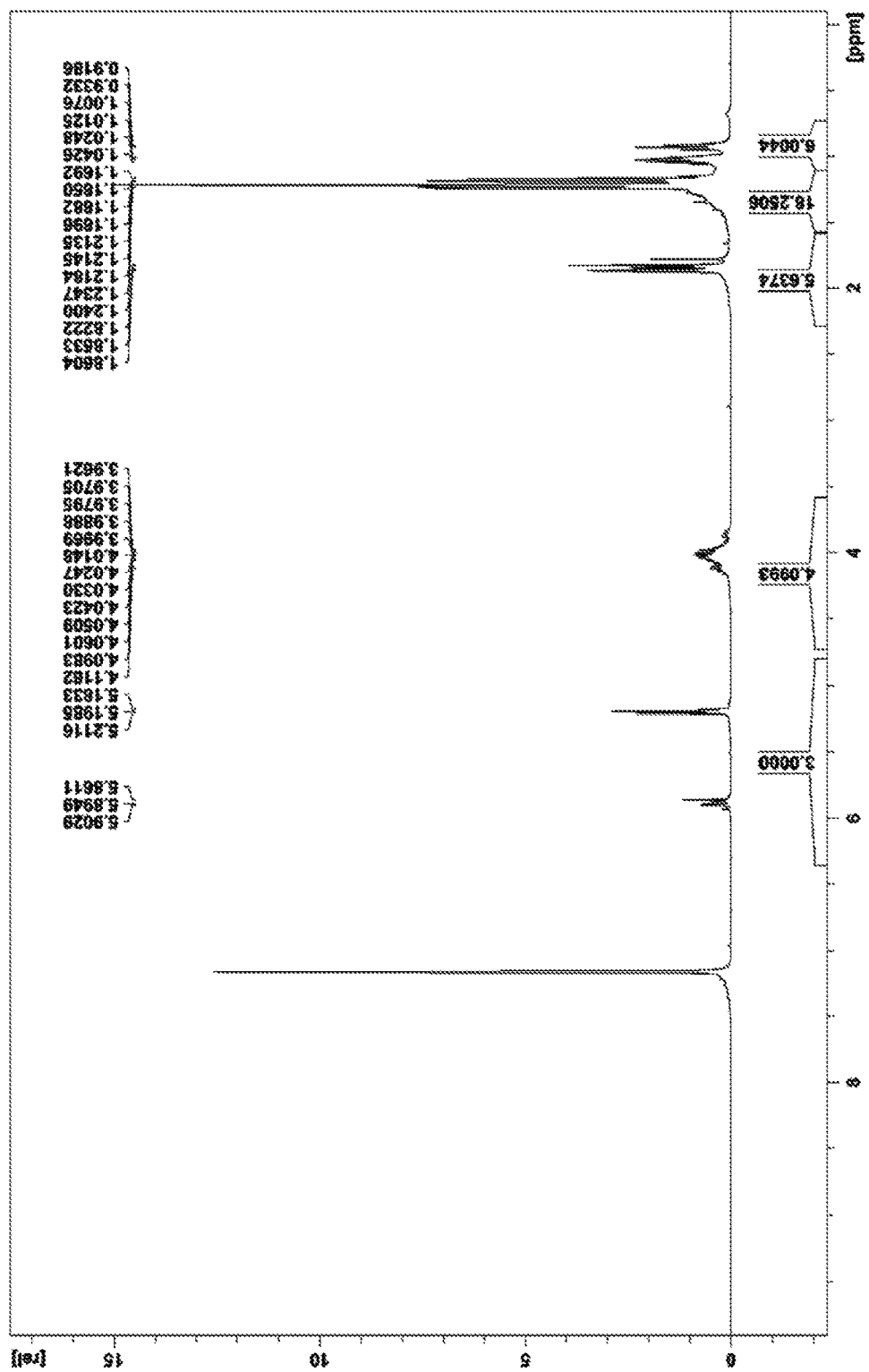
FIG. 3 is a $^1$HNMR chart of an aluminum chelate compound obtained in a third working example.

A measurement through ¹H-NMR spectrum was performed (FIG. 3) to confirm the average structure of the product generated.

¹H-NMR spectrum:
  δ 0.91 to 1.04 ppm (ratio of H: 6, —OCH₂CH₃)
  1.16 to 1.24 ppm (ratio of H: 18, —C(O)—C(CH₃)₃)
  1.82 to 1.86 ppm (ratio of H: 6, —C(O)—CH₃)
  3.96 to 4.11 ppm (ratio of H 4, —OCH₂CH₃)
  5.18 to 5.90 ppm (ratio of H 3, —C(O)CHC(O)—)

According to the results of the measurement through ¹H-NMR spectrum, it is regarded that the product obtained has the average structure of a mono (dipivaloylmethane) aluminum bis (ethylacetoacetate) chelate represented by the structure of the formula (9).

[Chemical formula 21]

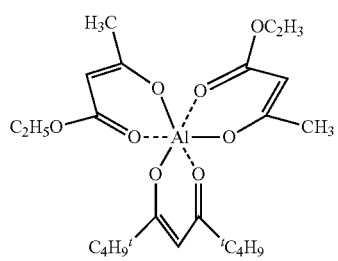

(9)

Working Example 4

A composition was obtained by mixing together 100 parts of a dimethylpolysiloxane having both terminal ends of its molecular chain blocked by trimethoxysilyl-ethylene groups and exhibiting a viscosity of 970 mPa·s; and 0.5 parts of the monoacetylacetonate aluminum bis (methylpivaloylacetoacetate) chelate prepared in the working example 1, in an environment where moisture was blocked, until a uniform consistency was achieved. Each freshly obtained composition was then pushed out on a glass Petri dish, and then exposed to an air of 50% RH at 23° C. The hardness of a cured product obtained after leaving the composition in such manner for 24 hours, was then measured using a hardness meter, a durometer A in compliance with JIS K-6249.

Working Example 5

A composition was obtained by mixing together 100 parts of a dimethylpolysiloxane having both terminal ends of its molecular chain blocked by trimethoxysilyl-ethylene groups and exhibiting a viscosity of 970 mPa·s; and 0.5 parts of the monoacetylacetonate aluminum bis (ethyl-4,4,4-trifluoroacetoacetate) chelate prepared in the working example 2, in an environment where moisture was blocked, until a uniform consistency was achieved. Each freshly obtained composition was then pushed out on a glass Petri dish, and then exposed to an air of 50% RH at 23° C. The hardness of a cured product obtained after leaving the composition in such manner for 24 hours, was then measured using a hardness meter, a durometer A in compliance with JIS K-6249.

Working Example 6

A composition was obtained by mixing together 100 parts of a dimethylpolysiloxane having both terminal ends of its molecular chain blocked by trimethoxysilyl-ethylene groups and exhibiting a viscosity of 970 mPa·s; and 0.5 parts of the monoacetylacetonate aluminum bis (methylpivaloylacetoacetate) chelate prepared in the working example 3, in an environment where moisture was blocked, until a uniform consistency was achieved. Each freshly obtained composition was then pushed out on a glass Petri dish, and then exposed to an air of 50% RH at 23° C. The hardness of a cured product obtained after leaving the composition in such manner for 24 hours, was then measured using a hardness meter, a durometer A in compliance with JIS K-6249.

Working examples 7 to 9

Compositions were obtained in the same manner as that of the working examples 4 to 6 except that there was employed 100 parts of a dimethylpolysiloxane having terminal ends of its branched chain blocked by trimethoxysilyl-ethane groups, instead of 100 parts of a dimethylpolysiloxane having terminal ends of its molecular chain blocked by trimethoxysilyl-ethylene groups.

Comparative Examples 1 and 2

Compositions were obtained in the same manner as that of the working example 4 except that 0.5 parts of a monoacetylacetonate aluminum bis (ethylacetoacetate) 76% isopropanol solution (product name: Aluminum Chelate D by Kawaken Fine Chemicals Co., Ltd.) or a monoacetylacetonate aluminum bis (2-ethylhexylacetoacetate), instead of 0.5 parts of the aluminum chelate compound synthesized in the working example 1.

Comparative Examples 3 and 4

Compositions were obtained in the same manner as that of the working example 7 except that 0.5 parts of a monoacetylacetonate aluminum bis (ethylacetoacetate) 76% isopropanol solution (product name: Aluminum Chelate D by Kawaken Fine Chemicals Co., Ltd.) or a monoacetylacetonate aluminum bis (2-ethylhexylacetoacetate), instead of 0.5 parts of the aluminum chelate compound synthesized in the working example 1.

These results are shown in Table 1.

TABLE 1

| | | Working example 4 | Working example 5 | Working example 6 | Comparative example 1 | Comparative example 2 | Working example 7 | Working example 8 | Working example 9 | Comparative example 3 | Comparative example 4 |
|---|---|---|---|---|---|---|---|---|---|---|---|
| Aluminum chelate compound | Working example 1 | 0.5 | | | | | 0.5 | | | | |
| | Working example 2 | | 0.5 | | | | | 0.5 | | | |
| | Working example 3 | | | 0.5 | | | | | 0.5 | | |
| | Aluminum chelate D | | | | 0.5 | | | | | 0.5 | |
| | Ethylhexyl | | | | | 0.5 | | | | | 0.5 |
| Dimethyl polysiloxane | Ethylene bridge | 100 | 100 | 100 | 100 | 100 | | | | | |
| | Ethane bridge | | | | | | 100 | 100 | 100 | 100 | 100 |
| | Curability | ○ | ○ | ○ | ○ | ○ | ○ | ○ | ○ | X | X |
| | Hardness/Duro · A | 17 | 15 | 24 | 13 | 4 | 6 | 1 | 11 | — | — |

According to the results shown in Table 1, it is obvious that each of the aluminum chelate compounds described in the working examples 1 to 3 has a curability higher than those of the corresponding monoacetylacetonate aluminum bis (ethylacetoacetate) 76% isopropanol solution (product name: Aluminum Chelate D by Kawaken Fine Chemicals Co., Ltd.) and monoacetylacetonate aluminum bis (2-ethylhexylacetoacetate) as listed as an example in the publication of Japanese Patent No. 3850969.

As for the room temperature-curable resin composition, working and comparative examples are shown below to describe the present invention in detail. However, the present invention is not limited to the following working examples. In the following specific examples, "parts" refers to "parts by mass," and a viscosity refers to a value measured by a rotary viscometer at 25° C.

Synthesis Example

Synthesis Example 1

Following is a method for synthesizing the dimethylpolysiloxane compound used in the working examples and having both terminal ends blocked by trimethoxysilyl-ethylene groups.
<Synthesis of Dimethylpolysiloxane Compound Having Ethynyl Groups at Both Terminal Ends>
Octamethylcyclotetrasiloxane of 3,050 g, 1,3-diethynyl-1,1,3,3-tetramethyldisiloxane of 32 g and a concentrated sulfuric acid ($H_2SO_4$) of 154 g were put in a 5,000 mL four-necked separable flask equipped with a mechanical stirrer, a thermometer and a dropping funnel. These ingredients were then stirred together at a room temperature (23° C.) for not less than 3 hours. Later, water ($H_2O$) of 66 g was added thereto, and the ingredients were further stirred together for not less than an hour. Next, toluene of 500 mL was added thereto to perform an isolation or separation of waste acid, and the toluene solution was later subjected to water washing until it had become neutral. The following polymer A exhibiting a viscosity of 935 mPa·s was obtained by stripping toluene and low molecular siloxane under a reduced pressure-condition of 150° C./8 mmHg.

[Chemical formula 22]

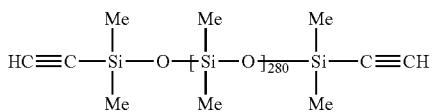

<Synthesis of Dimethylpolysiloxane Compound Having Both Terminal Ends Blocked by Trimethoxysilyl-Ethylene Groups>
The polymer A of 1,000 g, trimethoxysilane of 6.4 g and a chloroplatinic acid ($H_2PtCl_6·6H_2O$) of 0.5 g were placed in a 5,000 mL four-necked separable flask equipped with a mechanical stirrer, a thermometer and a dropping funnel. These ingredients were then stirred together at 70° C. for 3 hours. Later, the following polymer B exhibiting a viscosity of 970 mPa·s was obtained by performing stripping under a reduced pressure-condition of 120° C./20 mmHg.

[Chemical formula 23]

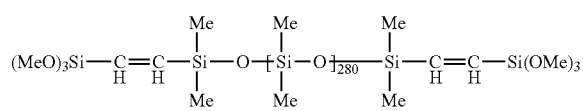

Working Example 10

A composition was obtained by mixing together 100 parts of a dimethylpolysiloxane (polymer B) having both terminal ends of its molecular chain blocked by trimethoxysilylethylene groups and exhibiting a viscosity of 970 mPa·s; and 0.5 parts of the monoacetylacetonate aluminum bis (ethylacetoacetate) 76% isopropanol solution (product name: Aluminum Chelate D by Kawaken Fine Chemicals Co., Ltd.), in an environment where moisture was blocked, until a uniform consistency was achieved.

Working Example 11

A composition was obtained by mixing together 100 parts of the dimethylpolysiloxane (polymer B) having both terminal ends of its molecular chain blocked by trimethoxysilyl-ethylene groups and exhibiting a viscosity of 970 mPa·s; and 0.5 parts of the monoacetylacetonate aluminum bis (ethyl-4,4,4-trifluoroacetoacetate) chelate prepared in the working example 2, in an environment where moisture was blocked, until a uniform consistency was achieved.

Working Example 12

A composition was obtained by mixing together 100 parts of the dimethylpolysiloxane (polymer B) having both terminal ends of its molecular chain blocked by trimethoxysilyl-ethylene groups and exhibiting a viscosity of 970 mPa·s; and 0.5 parts of the monoacetylacetonate aluminum bis (methylpivaloylacetoacetate) chelate prepared in the working example 1, in an environment where moisture was blocked, until a uniform consistency was achieved.

Working Example 13

A composition was obtained by mixing together 100 parts of the dimethylpolysiloxane (polymer B) having both terminal ends of its molecular chain blocked by trimethoxysilyl-ethylene groups and exhibiting a viscosity of 970 mPa·s; and 0.5 parts of the mono (dipivaloylmethane) aluminum bis (ethylacetoacetate) chelate prepared in the working example 3, in an environment where moisture was blocked, until a uniform consistency was achieved.

Working Example 14

A composition was obtained by mixing together 100 parts of a dimethylpolysiloxane having both terminal ends of its molecular chain blocked by hydroxyl groups and exhibiting a viscosity of 700 mPa·s; 6 parts of the following compound; and 0.5 parts of the monoacetylacetonate aluminum bis (methylpivaloylacetoacetate) chelate, in an environment where moisture was blocked, until a uniform consistency was achieved.

[Chemical formula 24]

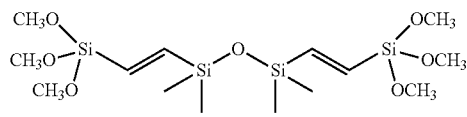

Comparative Examples 5 to 8

Compositions were obtained in the same manner as that of the working examples 10 to 13 except that there was used 100 parts of a dimethylpolysiloxane having the terminal ends of its molecular chain blocked by trimethoxysilyl-ethane groups, instead of 100 parts of a dimethylpolysiloxane having both terminal ends of its molecular chain blocked by trimethoxysilyl-ethylene groups.

Comparative examples 9 to 12

Compositions were obtained in the same manner as that of the working examples 10 to 13 except that there was used 100 parts of a dimethylpolysiloxane having the terminal ends of its molecular chain blocked by trimethoxysiloxy groups, instead of 100 parts of a dimethylpolysiloxane having both terminal ends of its molecular chain blocked by trimethoxysilyl-ethylene groups.

Comparative Example 13

A composition was obtained by mixing together 100 parts of the dimethylpolysiloxane (polymer B) having both terminal ends of its molecular chain blocked by trimethoxysilyl-ethylene groups and exhibiting a viscosity of 970 mPa·s; and 0.5 parts of a dioctyl tin dilaurate, in an environment where moisture was blocked, until a uniform consistency was achieved.

Comparative Example 14

A composition was obtained by mixing together 100 parts of the dimethylpolysiloxane (polymer B) having both terminal ends of its molecular chain blocked by trimethoxysilyl-ethylene groups and exhibiting a viscosity of 970 mPa·s; and 1 part of a diazabicycloundecene, in an environment where moisture was blocked, until a uniform consistency was achieved.

Test

A tack-free time of each composition prepared in the working examples 10 to 14 and the comparative examples 5 to 14, was measured.

Further, each freshly obtained composition of the working examples 10 to 14 and the comparative examples 5 to 14 was pushed out into the shape of a sheet having a thickness of 2 mm, followed by exposing the same to an air of 50% RH at 23° C. Next, the properties (initial properties) of a cured product obtained by leaving such sheet under the same atmosphere for 7 days were measured in accordance with JIS K-6249. Here, the hardness of the cured product was measured using a durometer A in compliance with JIS K-6249.

In addition, similar measurements were performed on a product obtained by storing the aforementioned cured product in a thermo-hygrostat of 85° C. and 85% RH for 100 hours. Moreover, similar measurements were also performed on a sheet of a thickness of 2 mm which had been made from a product prepared by placing each freshly obtained composition of the working examples 10 to 14 and the comparative examples 5 to 14 in a sealed container and then leaving the same there at 70° C. for 7 days. The results thereof are shown in the following tables.

TABLE 2

|  |  | Working example 10 | Working example 11 | Working example 12 | Working example 13 | Working example 14 |
|---|---|---|---|---|---|---|
| Initial | Hardness (Durometer A) | 19 | 23 | 21 | 30 | 21 |
|  | Elongation at break (%) | 120 | 110 | 70 | 60 | 105 |
|  | Tensile strength (MPa) | 0.32 | 0.35 | 0.22 | 0.32 | 0.35 |
| Endurance test 85° C., 85% RH | Hardness (Durometer A) | 23 | 28 | 28 | 29 | 25 |
|  | Elongation at break (%) | 135 | 85 | 80 | 60 | 105 |
|  | Tensile strength (MPa) | 0.42 | 0.33 | 0.32 | 0.28 | 0.28 |
| Preservation test 70° C., 7 days | Hardness (Durometer A) | 16 | 28 | 22 | 30 | 20 |
|  | Elongation at break (%) | 150 | 90 | 150 | 75 | 110 |
|  | Tensile strength (MPa) | 0.29 | 0.37 | 0.36 | 0.36 | 0.27 |
| Discoloration test | ΔE | 1.4 | 1.8 | 1.6 | 2.1 | 2.3 |

TABLE 3

|  |  | Comparative example 5 | Comparative example 6 | Comparative example 7 | Comparative example 8 |
|---|---|---|---|---|---|
| Initial | Hardness (Durometer A) | 3 | 12 | 2 | 17 |
|  | Elongation at break (%) | 100 | 225 | 290 | 95 |
|  | Tensile strength (MPa) | 0.05 | 0.14 | 0.05 | 0.23 |

TABLE 3-continued

|  |  | Comparative example 5 | Comparative example 6 | Comparative example 7 | Comparative example 8 |
|---|---|---|---|---|---|
| Endurance test 85° C., 85% RH | Hardness (Durometer A) | 9 | 6 | 21 | 9 |
|  | Elongation at break (%) | 245 | 130 | 100 | 195 |
|  | Tensile strength (MPa) | 0.15 | 0.11 | 0.24 | 0.12 |
| Preservation test 70° C., 7 days | Hardness (Durometer A) | 2 | 16 | 2 | 16 |
|  | Elongation at break (%) | 225 | 140 | 330 | 120 |
|  | Tensile strength (MPa) | 0.05 | 0.22 | 0.07 | 0.23 |
| Discoloration test | Δ E | 1.7 | 0.2 | 1.5 | 0.4 |

TABLE 4

|  |  | Comparative example 9 | Comparative example 10 | Comparative example 11 | Comparative example 12 |
|---|---|---|---|---|---|
| Initial | Hardness (Durometer A) | 1 | 2 | 1 | 7 |
|  | Elongation at break (%) | 50 | 140 | 110 | 90 |
|  | Tensile strength (MPa) | 0.02 | 0.06 | 0.05 | 0.12 |
| Endurance test 85° C., 85% RH | Hardness (Durometer A) | 3 | 24 | 6 | 21 |
|  | Elongation at break (%) | 260 | 170 | 130 | 120 |
|  | Tensile strength (MPa) | 0.06 | 0.58 | 0.06 | 0.30 |
| Preservation test 70° C., 7 days | Hardness (Durometer A) | 1 | 4 | 1 | 8 |
|  | Elongation at break (%) | 50 | 250 | 110 | 85 |
|  | Tensile strength (MPa) | 0.03 | 0.07 | 0.04 | 0.16 |
| Discoloration test | Δ E | 1.3 | 0.4 | 2.0 | 2.0 |

TABLE 5

|  |  | Comparative example 13 | Comparative example 14 |
|---|---|---|---|
| Initial | Hardness (Durometer A) | 26 | 26 |
|  | Elongation at break (%) | 90 | 75 |
|  | Tensile strength (MPa) | 0.36 | 0.38 |
| Endurance test 85° C., 85% RH | Hardness (Durometer A) | 27 | 27 |
|  | Elongation at break (%) | 95 | 80 |
|  | Tensile strength (MPa) | 0.38 | 0.37 |
| Preservation test 70° C., 7 days | Hardness (Durometer A) | 13 | 27 |
|  | Elongation at break (%) | 90 | 70 |
|  | Tensile strength (MPa) | 0.16 | 0.35 |
| Discoloration test | Δ E | 2.0 | 5.1 |

According to the results shown in the above tables, it is obvious that the fast curabilities observed in the working examples 10 to 14 were extremely higher than those of the corresponding comparative examples 5 to 14. Further, it is obvious that the working example 13 exhibited a preservation stability and durability that were significantly higher than those of the comparative example 8.

However, the present invention is not limited to the aforementioned working examples. The above working examples are simply shown as examples, and anything having a framework substantially identical to the technical idea(s) as set forth in the claims of the present application and bringing about similar effects shall be included in the technical scope of the present invention.

The invention claimed is:

1. A room temperature-curable resin composition comprising:
(A) 100 parts by mass of an alkoxysilyl-ethylene group terminated polymer having in one molecule at least one structure represented by the following general formula:

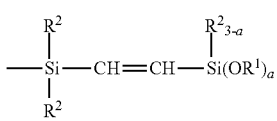

wherein each of $R^1$ and $R^2$ represents a substituted or unsubstituted monovalent hydrocarbon group having 1 to 12 carbon atoms, $R^1$ and $R^2$ being either identical to or different from each other; and a represents 2 or 3; and
(D) 0.001 to 15 parts by mass of an aluminum chelate compound having a β-ketoester and a β-diketone.

2. The room temperature-curable resin composition according to claim 1, wherein the component (D) comprises the aluminum chelate compound having a β-dicarbonyl compound represented by the following general formula (1):

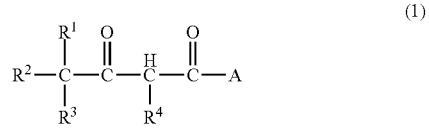

(1)

wherein each of $R^1$ to $R^3$ represents a halogen atom or a substituted or unsubstituted monovalent hydrocarbon group having 1 to 12 carbon atoms, $R^1$ to $R^3$ being either identical to or different from one another; $R^4$ represents a hydrogen atom or a substituted or unsubstituted monovalent hydrocarbon group having 1 to 12 carbon atoms; and A is a group represented by the following formula (2) or a group represented by —$OR^8$:

(2)

wherein each of $R^5$ to $R^7$ represents a halogen atom or a substituted or unsubstituted monovalent hydrocarbon group having 1 to 12 carbon atoms, $R^5$ to $R^7$ being either identical to or different from one another; and $R^8$ represents a substituted or unsubstituted monovalent hydrocarbon group having 1 to 5 carbon atoms,
provided that an average coordination number of said β-dicarbonyl compound represented by the general formula (1) to aluminum is 0.5 to 2.5.

3. The room temperature-curable resin composition according to claim 1, wherein the component (D) comprises the aluminum chelate compound having a β-ketoester represented by the following formula (3) and a β-diketone represented by the following formula (4):

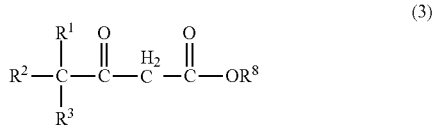

(3)

wherein each of $R^1$ to $R^3$ represents a halogen atom or a substituted or unsubstituted monovalent hydrocarbon group having 1 to 12 carbon atoms, $R^1$ to $R^3$ being either identical to or different from one another; and $R^8$ represents a substituted or unsubstituted monovalent hydrocarbon group having 1 to 5 carbon atoms

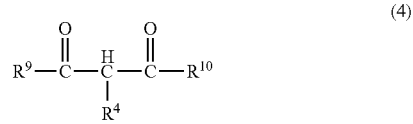

(4)

wherein each of $R^9$ and $R^{10}$ represents a substituted or unsubstituted monovalent hydrocarbon group having 1 to 12 carbon atoms, $R^9$ and $R^{10}$ being either identical to or different from each other; and $R^4$ represents a hydrogen atom or a substituted or unsubstituted monovalent hydrocarbon group having 1 to 12 carbon atoms, provided that an average molecular coordination number of said β-ketoester represented by the formula (3) to aluminum is 0.5 to 2.5, an average molecular coordination number of said diketone represented by the formula (4) to aluminum is 0.5 to 2.5, and an average molecular coordination number of a total of the formulae (3) and (4) is 3.0.

4. The room temperature-curable resin composition according to claim 1, wherein the component (D) comprises the aluminum chelate compound having a β-diketone represented by the following formula (5) and a β-ketoester represented by the following formula (6):

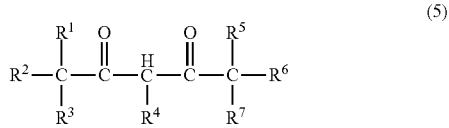

(5)

wherein each of $R^1$ to $R^3$ represents a halogen atom or a substituted or unsubstituted monovalent hydrocarbon group having 1 to 12 carbon atoms, $R^1$ to $R^3$ being either identical to or different from one another; $R^4$ represents a hydrogen atom or a substituted or unsubstituted monovalent hydrocarbon group having 1 to 12 carbon atoms; and each of $R^5$ to $R^7$ represents a halogen atom or a substituted or unsubstituted monovalent hydrocarbon group having 1 to 12 carbon atoms, $R^5$ to $R^7$ being either identical to or different from one another

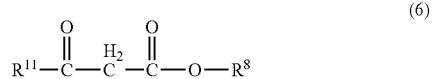

(6)

wherein $R^{11}$ represents a linear monovalent hydrocarbon group having 1 to 12 carbon atoms; and $R^8$ represents a substituted or unsubstituted monovalent hydrocarbon group having 1 to 5 carbon atoms, provided that an average molecular coordination number of said diketone represented by the formula (5) to aluminum is 0.5 to 2.5, an average molecular coordination number of said β-ketoester represented by the formula (6) to aluminum is 0.5 to 2.5, and an average molecular coordination number of a total of the formulae (5) and (6) is 3.0.

5. The room temperature-curable resin composition according to claim 1, wherein the component (D) comprises at least one aluminum chelate compound selected from the group consisting of a monoacetylacetonate aluminum bis (ethyl-4,4,4-trifluoroacetoacetate) chelate, a monoacetylacetonate aluminum bis (methylpivaloylacetoacetate) chelate, and a mono (dipivaloylmethane) aluminum bis (ethylacetoacetate) chelate.

6. The room temperature-curable resin composition according to claim 1, wherein the component (D) comprises monoacetylacetonate aluminum bis (ethylacetoacetate).

7. A room temperature-curable organopolysiloxane composition comprising:

(B) 100 parts by mass of a diorganopolysiloxane having in one molecule at least two silicon atoms, each silicon atom being bonded to a hydroxyl group and/or a hydrolyzable group;

(C) 0.1 to 30 parts by mass of an alkoxysilyl-ethylene group-containing compound having in one molecule at least one structure represented by the following general formula:

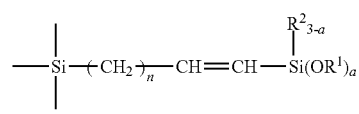

wherein each of $R^1$ and $R^2$ represents a substituted or unsubstituted monovalent hydrocarbon group having 1 to 12 carbon atoms, $R^1$ and $R^2$ being either identical to or different from each other; a represents 2 or 3; and n represents an integer of 0 to 10; and (D) 0.001 to 15 parts by mass of an aluminum chelate compound having a β-ketoester and a β-diketone.

8. The room temperature-curable organopolysiloxane composition according to claim 7, wherein the component (D) comprises the aluminum chelate compound having a β-dicarbonyl represented by the following general formula (1):

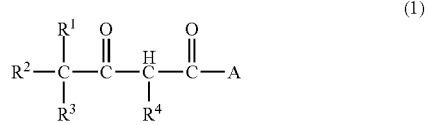

(1)

wherein each of $R^1$ to $R^3$ represents a halogen atom or a substituted or unsubstituted monovalent hydrocarbon group having 1 to 12 carbon atoms, $R^1$ to $R^3$ being either identical to or different from one another; $R^4$ represents a hydrogen atom or a substituted or unsubstituted monovalent hydrocarbon group having 1 to 12 carbon atoms; and A is a group represented by the following formula (2) or a group represented by —$OR^8$:

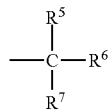
(2)

wherein each of $R^5$ to $R^7$ represents a halogen atom or a substituted or unsubstituted monovalent hydrocarbon group having 1 to 12 carbon atoms, $R^5$ to $R^7$ being either identical to or different from one another; and $R^8$ represents a substituted or unsubstituted monovalent hydrocarbon group having 1 to 5 carbon atoms, provided that an average coordination number of said β-dicarbonyl compound represented by the general formula (1) to aluminum is 0.5 to 2.5.

9. The room temperature-curable organopolysiloxane composition according to claim 7, wherein the component (D) comprises the aluminum chelate compound having a β-ketoester represented by the following formula (3) and a β-diketone represented by the following formula (4):

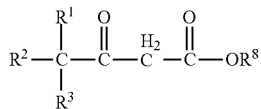
(3)

wherein each of $R^1$ to $R^3$ represents a halogen atom or a substituted or unsubstituted monovalent hydrocarbon group having 1 to 12 carbon atoms, $R^1$ to $R^3$ being either identical to or different from one another; and $R^8$ represents a substituted or unsubstituted monovalent hydrocarbon group having 1 to 5 carbon atoms

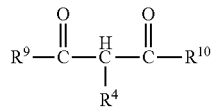
(4)

wherein each of $R^9$ and $R^{10}$ represents a substituted or unsubstituted monovalent hydrocarbon group having 1 to 12 carbon atoms, $R^9$ and $R^{10}$ being either identical to or different from each other; and $R^4$ represents a hydrogen atom or a substituted or unsubstituted monovalent hydrocarbon group having 1 to 12 carbon atoms, provided that an average molecular coordination number of said β-ketoester represented by the formula (3) to aluminum is 0.5 to 2.5, an average molecular coordination number of said diketone represented by the formula (4) to aluminum is 0.5 to 2.5, and an average molecular coordination number of a total of the formulae (3) and (4) is 3.0.

10. The room temperature-curable organopolysiloxane composition according to claim 7, wherein the component (D) comprises the aluminum chelate compound having a β-diketone represented by the following formula (5) and a β-ketoester represented by the following formula (6):

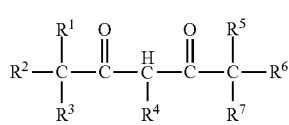
(5)

wherein each of $R^1$ to $R^3$ represents a halogen atom or a substituted or unsubstituted monovalent hydrocarbon group having 1 to 12 carbon atoms, $R^1$ to $R^3$ being either identical to or different from one another; $R^4$ represents a hydrogen atom or a substituted or unsubstituted monovalent hydrocarbon group having 1 to 12 carbon atoms; and each of $R^5$ to $R^7$ represents a halogen atom or a substituted or unsubstituted monovalent hydrocarbon group having 1 to 12 carbon atoms, $R^5$ to $R^7$ being either identical to or different from one another

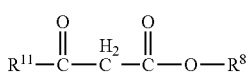
(6)

wherein represents a linear monovalent hydrocarbon group having 1 to 12 carbon atoms; and $R^8$ represents a substituted or unsubstituted monovalent hydrocarbon group having 1 to 5 carbon atoms, provided that an average molecular coordination number of said diketone represented by the formula (5) to aluminum is 0.5 to 2.5, an average molecular coordination number of said β-ketoester represented by the formula (6) to aluminum is 0.5 to 2.5, and an average molecular coordination number of a total of the formulae (5) and (6) is 3.0.

11. The room temperature-curable organopolysiloxane composition according to claim 7, wherein the component (D) comprises at least one aluminum chelate compound selected from the group consisting of
a monoacetylacetonate aluminum bis (ethyl-4,4,4-trifluoroacetoacetate) chelate,
a monoacetylacetonate aluminum bis (methylpivaloylacetoacetate) chelate, and
a mono (dipivaloylmethane) aluminum bis (ethylacetoacetate) chelate.

12. The room temperature-curable organopolysiloxane composition according to claim 7, wherein the component (D) comprises monoacetylacetonate aluminum bis (ethylacetoacetate).

13. A molded product obtained by curing the room temperature-curable resin composition of claim 1.

14. A molded product obtained by curing the room temperature-curable resin composition of claim 7.

15. A coating, adhesive or sealing agent comprising the room temperature-curable resin composition of claim 1.

16. A coating, adhesive or sealing agent comprising the room temperature-curable resin composition of claim 7.

* * * * *